United States Patent
Bhujwalla et al.

(10) Patent No.: US 12,161,727 B2
(45) Date of Patent: Dec. 10, 2024

(54) METHOD TO SYNTHESIZE A BIODEGRADABLE DEXTRAN FOR AGENT DELIVERY

(71) Applicant: THE JOHNS HOPKINS UNIVERSITY, Baltimore, MD (US)

(72) Inventors: Zaver M. Bhujwalla, Baltimore, MD (US); Zhihang Chen, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 928 days.

(21) Appl. No.: 17/059,298

(22) PCT Filed: May 23, 2019

(86) PCT No.: PCT/US2019/033649
§ 371 (c)(1),
(2) Date: Nov. 27, 2020

(87) PCT Pub. No.: WO2019/231799
PCT Pub. Date: Dec. 5, 2019

(65) Prior Publication Data
US 2021/0138085 A1 May 13, 2021

Related U.S. Application Data

(60) Provisional application No. 62/677,299, filed on May 29, 2018.

(51) Int. Cl.
*A61K 47/69* (2017.01)
*A61K 47/61* (2017.01)
*A61P 35/00* (2006.01)
*C12N 15/113* (2010.01)

(52) U.S. Cl.
CPC .......... *A61K 47/6939* (2017.08); *A61K 47/61* (2017.08); *A61P 35/00* (2018.01); *C12N 15/1137* (2013.01); *C12N 2310/14* (2013.01); *C12N 2320/32* (2013.01)

(58) Field of Classification Search
CPC ....... A61K 47/61; A61K 47/6939; C08L 5/00; C08L 5/02
See application file for complete search history.

(56) References Cited

PUBLICATIONS

Chen, Z. et al. "Degradable Dextran Nanopolymer as a Carrier for Choline Kinase (ChoK) siRNA Cancer Therapy", Feb. 22, 2016, Nanomaterials, vol. 6, 34. (Year: 2016).*
Cui, L. et al. "Conjugation Chemistry through Acetals toward a Dextran-Based Delivery System for Controlled Release of siRNA", Sep. 7, 2012, Journal of the American Chemical Society, vol. 134, pp. 15840-15848. (Year: 2012).*
Jiang, B.; et al. "Ibuprofen-loaded nanoparticles prepared by a co-precipitation method and their release properties", 2005, International Journal of Pharmaceutics, vol. 304, pp. 220-230. (Year: 2005).*
Abioye, A. O.; et al. "Controlled Electrostatic Self-Assembly of Ibuprofen-Cationic Dextran Nanoconjugates Prepared by low Energy Green Process—a Novel Delivery Tool for Poorly Soluble Drugs", 2015, Pharmaceutical Research, vol. 32, pp. 2110-2131. (Year: 2015).*
Wang, J.; et al. "Visible light-switched cytosol release of siRNA by amphiphilic fullerene derivative to enhance RNAi efficacy in vitro and in vivo" 2017, Acta Biomaterialia, vol. 59, pp. 1580-169. (Year: 2017).*
Andreoni, A.; et al. "Time-Resolved Fluorescence Studies of Fullerene Derivatives" 2013, J. Phys. Chem. B, vol. 117, pp. 7203-7209. (Year: 2013).*
International Search Report and Written Opinion in corresponding International Application No. PCT/US2019/033649 mailed on Sep. 26, 2019, 6 pages.
Chen et al., "Acid-degradable Dextran as an Image Guided siRNA Carrier for COX-2 Downregulation" Theranostics 2018; 8(1):1-12, 12 pages.
Sun et al., "Functional Groups Affect Physical and Biological Properties of Dextran-Based Hydrogels", J. Biomedical Materials Res. Pary A 2009; 93(3):1080-90, 11 pages.

* cited by examiner

*Primary Examiner* — Eric Olson
*Assistant Examiner* — Benjamin M Brandsen
(74) *Attorney, Agent, or Firm* — MH2 Technology Law Group LLP

(57) ABSTRACT

Disclosed are delivery compositions and methods of making and using these compositions. The delivery compositions comprise a collection of polysaccharide degradable dextran nanopolymers comprising one or more amines having 25% or less cross linking. The polysaccharide degradable dextran nanopolymers may be sphere shaped with a radius in the range of 5 nm to 100 nm.

14 Claims, 12 Drawing Sheets

METHOD TO SYNTHESIZE A BIODEGRADABLE DEXTRAN FOR AGENT DELIVERY

REFERENCE TO RELATED APPLICATIONS

This application is a national stage entry from International Application No. PCT/US2019/033649, filed on May 23, 2019, published as International Publication No. WO 2019/231799 A1 on Dec. 5, 2019, and claims the benefit of U.S. Provisional Patent application 62/677,299, filed May 29, 2018, all of which are hereby incorporated by reference in their entirety for all purposes as if fully set forth herein.

BACKGROUND OF THE INVENTION

As a molecular-based therapeutic strategy, specific gene knockdown using small interfering RNA (siRNA) is being actively investigated for the treatment of many diseases such as cancer, inflammation, diabetes, and neurodegenerative diseases. siRNA can enter the RNA-induced silencing complex (RISC) to induce enzyme-catalyzed degradation of the complementary mRNA in diseased cells, thus disrupting specific molecular pathways. siRNA-mediated silencing of target mRNAs has the potential to down-regulate pathways not accessible with pharmacological agents, without non-specific side-effects that are frequently associated with pharmacological agents. The down-regulation of cyclooxygenase-2 (COX-2) using siRNA is one example where the application of this technology would be of significant importance for a critical target that has not been fully utilized due to the side-effects of pharmacological inhibitors. The two major isoforms of COX, COX-1 and COX-2, transform arachidonic acid into prostaglandins (PGs) that are important biological mediators of inflammation. COX-1 is constitutively expressed in normal tissues, whereas the inducible form, COX-2, shows high expression in inflammatory tissues and many cancers. In cancer, COX-2 has been found to play an important role in invasion and metastasis in prostate, colorectal, and breast cancer. Consequently, COX-2 as a target has attracted significant pharmaceutical interest for multiple degenerative diseases and cancer. Unlike pharmacological COX-2 inhibitors that have significant side-effects, COX-2 siRNA can provide specific and effective down-regulation of COX-2.

Although siRNA is a rapidly emerging class of new therapeutic molecules for the treatment of inherited and acquired diseases, there are some barriers in achieving efficient siRNA therapy. Because of the high molecular weight and negative charge in the form of phosphate, free siRNA cannot enter cells efficiently. Further, naked siRNA has a short lifetime in circulating blood due to nucleases and the innate immune system, requiring the use of suitable carriers for successful siRNA therapy. The lack of suitable biocompatible carriers that can achieve effective siRNA delivery and downregulate target genes has, however, limited human translational applications of siRNA therapy. A large number of carriers such as viral vectors, cationic lipids, and polymers have been investigated for siRNA delivery. Viral vectors raise safety concerns due to off-target immunogenicity, inflammatory response, and toxicity. In addition, effective COX-2 downregulation using carriers delivering COX-2 siRNA has remained a major challenge because COX-2 is easily induced by extrinsic chemicals, or by artificial cationic polymers with a high density of positive charges. New carriers of bioactive and/or pharmaceutical agents are needed to develop safe and effective drugs for the treatment and prevention of disease.

SUMMARY OF THE INVENTION

One embodiment of the present invention is a method of making a delivery composition. The steps of the method include oxidizing dextran to form low oxidation dextran wherein less than 10% of the dextran is oxidized. The oxidation step may be performed in a PBS solution at pH 7.0, for example. Adding excess small diamine molecules to the low oxidation dextran PBS solution to form a Schiff base. An excess of small diamine molecules may be in the range of greater or equal to 20 equivalents of the dextran. Reducing the Schiff base to an amine functional oxidized dextran by the addition of sodium cyanoborohydride. Incubating the amine functional oxidized dextran with one or more labels that bind to some amine groups of the amine functional oxidized dextran forming a labeled amine functional oxidized dextran comprising labeled amines and unreacted amines. Blocking the unreacted amines with a blocking agent to form a blocked dextran. Incubating the blocked dextran with small polyamines molecules comprising a dimethyl acetal group forming a dextran comprising one or more cleavable amine groups. Conjugating the dextran comprising one or more cleavable amine groups with the one or more labels at the cleavable amine group. Forming a delivery composition of the present invention.

Suitable labels used in the present invention include targeting moieties, imaging reporters such as MR imaging reporters, optical imaging reporters, NIR imaging reporters, nuclear imaging reporters, or a combination thereof. The labels used in the present invention may be used in one or more process steps and the labels may be the same or different in each step requiring a label. For example, labels that are incubated with the amine functional oxidized dextran may be different from the labels that are conjugated with the dextran comprising one or more cleavable amine groups.

An example of a suitable blocking agent used in the present invention is N-succinimidyl acetate. An example of a small polyamine molecule comprising a dimethyl acetal group used in the present invention is N-(2-(bis(2-aminoethyl)amino)ethyl)-4-(4-(dimethoxymethyl)-2-methoxyphenoxy)butanamide. The small polyamine molecule comprising a dimethyl acetal group may bind to blocked dextran through acetal bonds.

Another embodiment of the present invention is delivery composition comprising a collection of polysaccharide degradable dextran nanopolymers comprising one or more amines. The collection of nanopolymer comprises 25% or less cross linking. Delivery compositions of the present invention may further comprise spheres of the polysaccharide degradable dextran nanopolymers with a radius in the range of 5 nm to 100 nm. In addition, the collection of polysaccharide degradable dextran nanopolymers may be positively charged. The delivery compositions of the present invention may further comprise an agent, such as a nucleic acid, chemical, protein, antibody, peptide, or a combination thereof, as examples. The agent may be an siRNA such as a cyclooxygenase-2 (COX-2) siRNA. The agent maybe negatively charged and binds electrostatically with one or more amine groups on the polysaccharide degradable dextran nanopolymers. The delivery composition of claim 6 may comprise a pharmaceutically acceptable carrier and be a pharmaceutical composition.

Another embodiment of the present invention is a method of treating or preventing a disease in a subject comprising the following steps. Administering a pharmaceutical composition to a subject that comprises a collection of nanopolymers of polysaccharide comprising one or more amines, an agent, and wherein the collection of nanopolymers comprises 25% or less cross linking. The subject has a disease or is at risk of getting a disease and treating or preventing the disease in the subject when compared to a reference subject who was not administered the pharmaceutical composition. Agents used in the present invention may be bound to the one or more amine groups on the polysaccharide polymer. Agents of the present invention maybe released from the polysaccharide polymer when acetal bonds on the nanopolymers are cleaved under acid conditions, for example in range of a pH of 6.5 or lower. The methods of the present invention maybe used to treat or prevent a disease such as cancer, for example by inhibiting solid tumor growth in a subject. The methods of the present invention may be used to deliver a COX-2 siRNA to a subject that downregulates COX-2 expression in a subject's tumor inhibiting solid tumor growth.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

The term "activity" refers to the ability of a gene to perform its function such as Cox 2 (a cyclooxygenase) catalyzing the formation of prostanoids, including thromboxane and prostaglandins such as prostacycline.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels."

By "analog" is meant a molecule, including nucleic acids, that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

By "disease" is meant any condition or disorder that damages or interferes with the normal function of a cell, tissue, or organ. Examples of diseases include cancer.

By "effective amount" is meant the amount of a required to ameliorate the symptoms of a disease relative to an untreated patient. The effective amount of active compound (s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The term "express" refers to the ability of a gene to express the gene product including for example its corresponding mRNA or protein sequence (s).

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

The term, "obtaining" as in "obtaining an agent" includes synthesizing, purchasing, or otherwise acquiring the agent.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins.

By "reduces" is meant a negative alteration of at least 10%, 25%, 50%, 75%, or 100%.

A "reference" refers to a standard or control conditions such as a sample (human cells) or a subject that is a free, or substantially free, of an agent such as one or more inhibitors of COX, such as COX 2 as an example.

A "reference sequence" is a defined sequence used as a basis for sequence comparison. A reference sequence may be a subset of or the entirety of a specified sequence; for example, a segment of a full-length cDNA, gene, or RNA sequence, or the complete cDNA, gene, or RNA sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or there between.

As used herein, the term "sensitivity" is the percentage of subjects with a particular disease.

As used herein, the term "specificity" is the percentage of subjects correctly identified as having a particular disease i.e., normal or healthy subjects. For example, the specificity is calculated as the number of subjects with a particular disease as compared to non-cancer subjects (e.g., normal healthy subjects).

By "specifically binds" is meant a compound such as a nucleic acid including a siRNA that recognizes and binds a nucleic acid sequence in vitro or in-vivo, but which does not substantially recognize and bind other molecules in a sample, for example, a biological sample.

As used herein, the term "subject" is intended to refer to any individual or patient to which the method described herein is performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

Such treatment (surgery and/or chemotherapy) will be suitably administered to subjects, particularly humans, suffering from, having, susceptible to, or at risk for cancer or disease, disorder, or symptom thereof. Determination of those subjects "at risk" can be made by any objective or subjective determination by a diagnostic test or opinion of a subject or health care provider (e.g., genetic test, enzyme or protein marker, a marker (as defined herein), family history, and the like).

Abbreviations

COX-2: Cyclooxygenase-2; siRNA: small interfering RNA; RISC: RNA-induced silencing complex; TNBS: trinitrobenzene sulfonic acid; DLS: dynamic light scattering; TEM: transmission electronic microscopy; N/P ratio: nitrogen/phosphate ratio; FITC: fluorescein isothiocyanate; qRT-PCR: quantitative reverse transcription polymerase chain reaction; TPA: 12-O-tetradecanoylphorbol-13-acetate; $PGH_2$: prostaglandin $H_2$; $PGG_2$: prostaglandin $G_2$; $PGE_2$: prostaglandin $E_2$; PEI: polyethylenimine; EPR effect: enhanced permeability and retention effect; SCID mice: severe combined immunodeficient mice; HPRT1: hypoxanthine phosphoribosyl transferase 1; GAPDH: glyceraldehyde 3-phosphate dehydrogenase.

DETAILED DESCRIPTION OF THE INVENTION

Figures 1A, 1B, 1C, 1D:
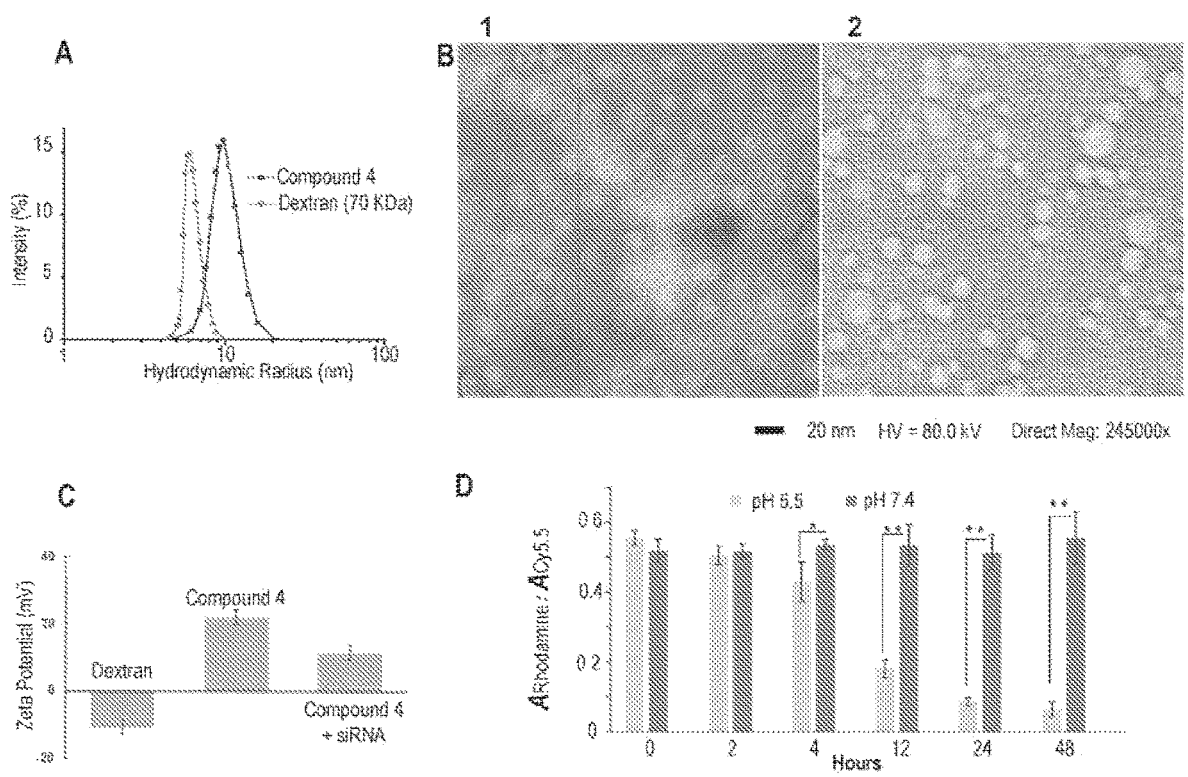
FIG. 1A-1D: (A) Hydrodynamic radius of dextran and compound 4. (B) TEM image of compound 4 (B1) and COX-2 siRNA/compound 4 complex (B2). (Negative staining with phosphotungstic acid (PTA), scale bar is 20 nm). (C) Zeta potential of dextran and compound 4. (n=3, values represent mean±SD.) (D) The ratio of rhodamine absorbance to Cy5.5 absorbance at pH 5.5 and pH 7.4 buffer at different time points. (n=3, values represent mean±SD, \*\*: P<0.01, \*: P<0.05).

Effective COX-2 downregulation using carriers delivering COX-2 siRNA has remained a major challenge because COX-2 is easily induced by extrinsic chemicals, or by artificial cationic polymers with a high density of positive charges. There are few, if any, reports about the use of artificial cationic polymers to downregulate COX-2 in cancer cells in vivo and in vitro. Because increase of COX-2 expression can increase aggressiveness, nanoparticles used in oncological applications should ideally not induce COX-2. Therefore, excellent biocompatibility of a cationic polymer as a carrier is vital for successful siRNA delivery in general, and COX-2 siRNA delivery in particular. Such a cationic polymer should be biodegradable and should rapidly release siRNA in cancer cells. Small molecules that are products of polymer degradation are more rapidly metabolized than cationic polymers, resulting in a shorter residence time that minimizes side-effects. Biodegradation triggered within cells provides a strategy to resolve the coexistence of two conflicting requirements in the rational design of polymeric vectors: condensation and release of siRNA. Cationic polymers possess the ability to form a compact polymer complex with siRNA and to transfer siRNA into cells efficiently; however, such strong complexation impedes the release of siRNA for initiation of post-transcriptional silencing. Once the degradation of the polymer occurs in cells, it loses the ability to compact the siRNA resulting in rapid siRNA release. This makes rapid polymer degradation once inside cells, a highly desirable attribute for effective siRNA delivery.

Here the inventors developed a novel method to efficiently synthesize a multiple imaging reporters labeled biodegradable dextran to use as an efficient cationic nanopolymer carrier for COX-2 siRNA delivery. As a homopolysaccharide of glucose, dextran has been used as a drug carrier in human applications due to its biodegradability, wide availability, and ease of modification. The potential applications of dextran, such as in micelles and hydrogels for siRNA delivery, have recently been demonstrated. In the present invention, amine groups that electrostatically bind siRNA were conjugated to the dextran platform through acetal bonds. Acetal bonds are attractive because they are cleaved under acidic conditions that occur within endocytotic compartments, to rapidly release the amine groups. Rhodamine was conjugated to the amine groups to detect release of these groups from the dextran scaffold and their removal from cancer cells following cleavage of the acetal bonds, while the dextran scaffold was labeled with Cy5.5. With these imaging reporters, the distribution and degradation of this dextran carrier in vitro and in vivo were investigated and visualized by optical imaging, for the first time. The rapid release of amine groups minimized the proinflammatory side-effects of the positively charged amine group, making this cationic nanopolymer a useful carrier for siRNA delivery to downregulate COX-2 expression in cancer cells and tumors. Since increased COX-2 expression can result in an aggressive phenotype in cancer cells, identification of a nanopolymer that does not increase COX-2 expression provides a clear path for translational applications of siRNA delivery in cancer.

Synthesis and Characterization of Nanoplex

Figure 7:
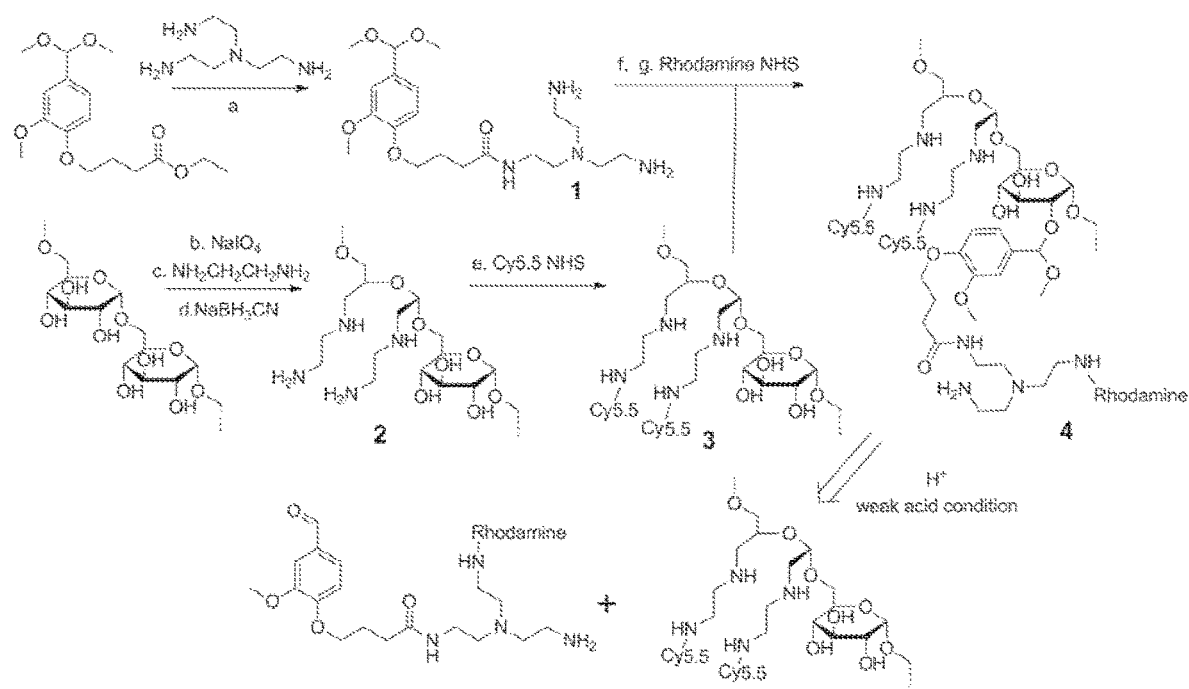
FIG. 7: Synthesis procedure and degradation mechanism of the dextran siRNA carrier under acidic conditions. (a) 100° C., overnight. (b) pH 5.0, room temperature, 4 h. (c) PBS pH 7.0 buffer, room temperature, 2 h. (d) PBS pH 7.0 buffer, room temperature, overnight. (e) HEPES buffer, pH 8.4, room temperature, 2 h, (f) p-toluenesulfonic acid, 4 Å molecular sieves, 65° C., overnight. (g) HEPES buffer, pH 8.4, room temperature, 2 h.

The synthesis of the dextran polymer is presented in FIG. 7. Dextran (70 kDa) was oxidized to form dextran with an aldehyde functional group. The actual oxidation degree determined by the trinitrobenzene sulfonic acid (TNBS) assay was 3.1±0.2%. Excess ethylenediamine (>20 eq) was added to the oxidized dextran PBS solution (pH 7.0) to form the Schiff base. This unstable Schiff base was reduced to a stable nitrogen-carbon bond compound by sodium cyanoborohydride. Cy5.5 was conjugated to the dextran platform (1.1 Cy5.5 molecule per dextran molecule), and the unreacted amine groups were blocked by N-succinimidyl acetate to prevent further side-reactions, such as the conjugation between rhodamine and unreacted amine groups, during further modifications. The Cy5.5 labeled dextran scaffold was reacted with an excess of compound 1 to attach the amine groups to the dextran polymer through the acetal bonds. $^1$H NMR spectra indicated that the functionalized degree of glucose residues was ~0.5. Finally, rhodamine was conjugated to the cleavable amine groups (1.2 rhodamine molecule per dextran molecule).

Although the use of acid degradable dextran with acetal bonds as an siRNA carrier has been previously reported, limitations in the synthesis prevented further modification of the dextran scaffold. In the previously reported method, the formation of acetal bonds preceded the introduction of amine functional groups, resulting in problems arising from the premature introduction of acetal bonds. Primarily, in the reported method, 20-40 equivalent amine molecules per acetal bond were reacted with the dextran platform at 50° C. for two weeks to conjugate the amine functional groups. With concentrated alkali, long reaction times, and high temperature, this reaction condition was not compatible with attaching several functional groups to the dextran scaffold. In fact, the cyanine and rhodamine dyes used as imaging probes in our nanopolymer were not stable under this reaction condition. As a result, this previously reported method could not be used to label imaging reporters to the dextran platform to investigate distribution and degradation in cells and in vivo. Additionally, attaching amines during the final step would cause crosslinking between the dextran molecules, affecting the size distribution of the dextran polymer. To achieve efficient binding with siRNA, a large number of small molecules with multi amine functional groups were conjugated to the dextran scaffold by reaction with ester. If the amine groups in one molecule reacted with different dextran scaffolds, this would induce crosslinking between the dextrans. Use of the previously reported method resulted in a wider size distribution of the dextran nanopolymer, and there were some particles with abnormally large sizes. The novel cationic dextran polymer synthesis method of the present invention overcame both limitations of the previous method, demonstrating the ability to modify the dextran scaffold with a variety of functional groups such as imaging reporters and targeting moieties, but avoiding crosslinking of the dextran scaffold. Using this novel synthesis method, the inventor's synthesized multi-imaging reporter labeled degradable dextran nanopolymer as a siRNA carrier; the imaging reporters allowed detection of degradation, distribution and metabolism of the nanocarrier in vitro and in vivo.

Figure 8:
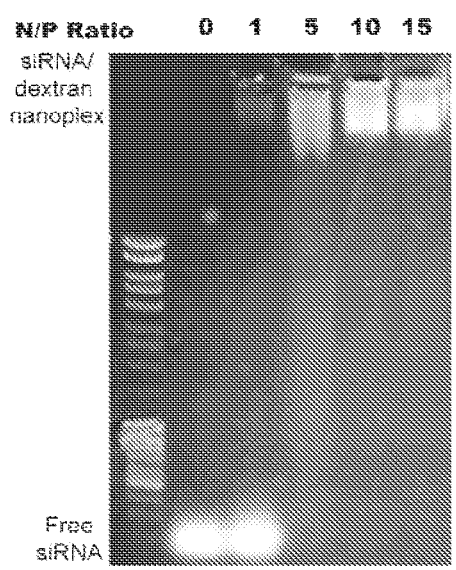
FIG. 8: Electrophoretic gel mobility shift assay of stability of dextran-siRNA nanoplex.
Figure 9:
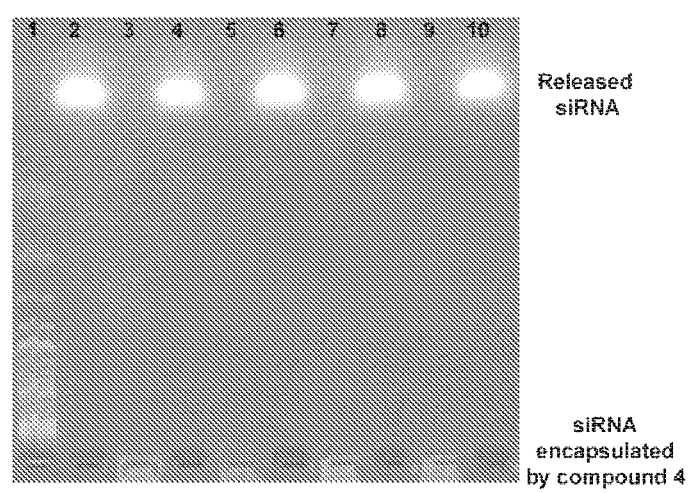
FIG. 9: Stability of siRNA encapsulated in siRNA/compound 4 nanoplex in fresh mouse serum (Sigma-Aldrich, St. Louis, MO) or human serum (Sigma-Aldrich, St. Louis, MO). (Lane 1: Ladder; Lane 2: COX-2 siRNA control; Lane 3: siRNA/compound 4 nanoplex in fresh mouse serum for 24 h; Lane 4: siRNA/compound 4 nanoplex in fresh mouse serum for 24 h with SDS; Lane 5: siRNA/compound 4 nanoplex in fresh mouse serum for 72 h; Lane 6: siRNA/compound 4 nanoplex in fresh mouse serum for 72 h with SDS; Lane 7: siRNA/compound 4 nanoplex in fresh human serum for 24 h; Lane 8: siRNA/compound 4 nanoplex in fresh human serum for 24 h with SDS; Lane 9: siRNA/compound 4 nanoplex in fresh human serum for 72 h; Lane 10: siRNA/compound 4 nanoplex in fresh human serum for 72 h with SDS.
Figure 10:
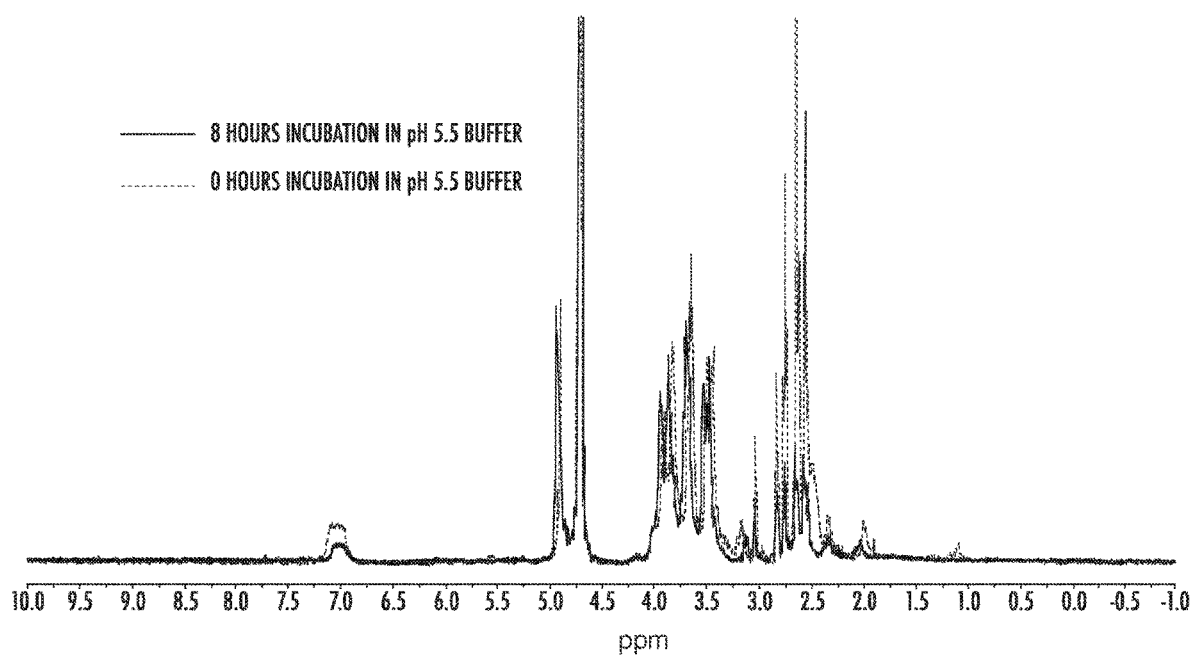
FIG. 10: $^1$H NMR spectra of compound 4 before and after incubation in pH 5.5 buffer. The intensity of peaks was normalized to the peak of dextran at 4.9 ppm

Dynamic light scattering (DLS) was performed to investigate the hydrodynamic radius of the dextran carriers (FIG. 1A). The radius of dextran (70 kDa) was ~6 nm, and the radius increased to ~9.8 nm after modifications. This result was also confirmed by transmission electronic microscopy (TEM) (FIG. 1B) that identified a diameter of ~20 nm. After binding with COX-2 siRNA, the size of the nanoplex did not change significantly, and remained at a radius of ~9.9 nm. With the attachment of cleavable amino groups, the zeta potential of compound 4 increased to 22.2±2.3 mV, compared to −12.3±0.4 mV of natural dextran. This positive charge was sufficient to achieve electrostatic binding with siRNA. The inventors also examined the complexation between siRNA and the amino-dextran using gel electrophoresis. Compound 4 formed firm complexes with siRNA at nitrogen/phosphate (N/P) ratios of 15 within 20 min incubation in PBS solution (pH 7.4) (FIG. 8). With this N/P ratio the COX-2 siRNA in this nanoplex was stable in mouse and human serum for up to 8 h of incubation (FIG. 9). The zeta potential of compound 4/siRNA nanoplex at N/P ratio of 15 was 12.2±1.7 mV. Cytotoxicity of compound 4 evaluated using an MTT assay showed the absence of toxicity in MDA-MB-231 human breast cancer cells with concentrations as high as 100 μg/mL (FIG. 10).

Figure 11:
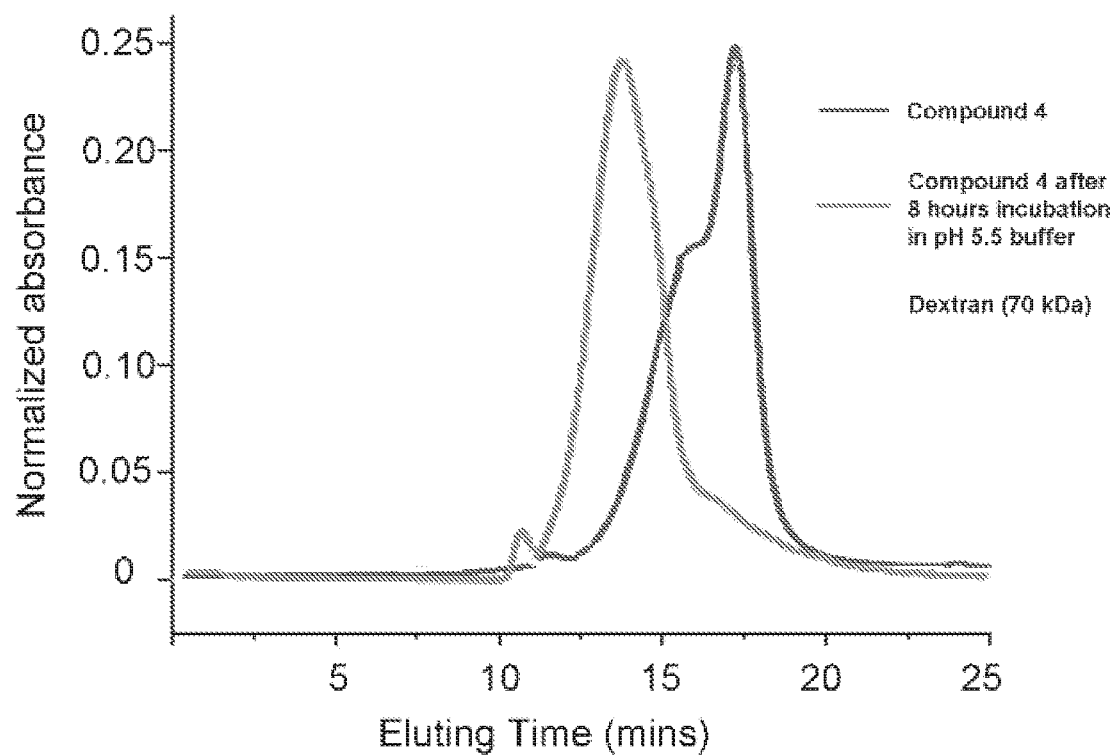
FIG. 11: The effluent peak of dextran and compound 4 before and after incubation in pH 5.5 buffer.
Figure 12:
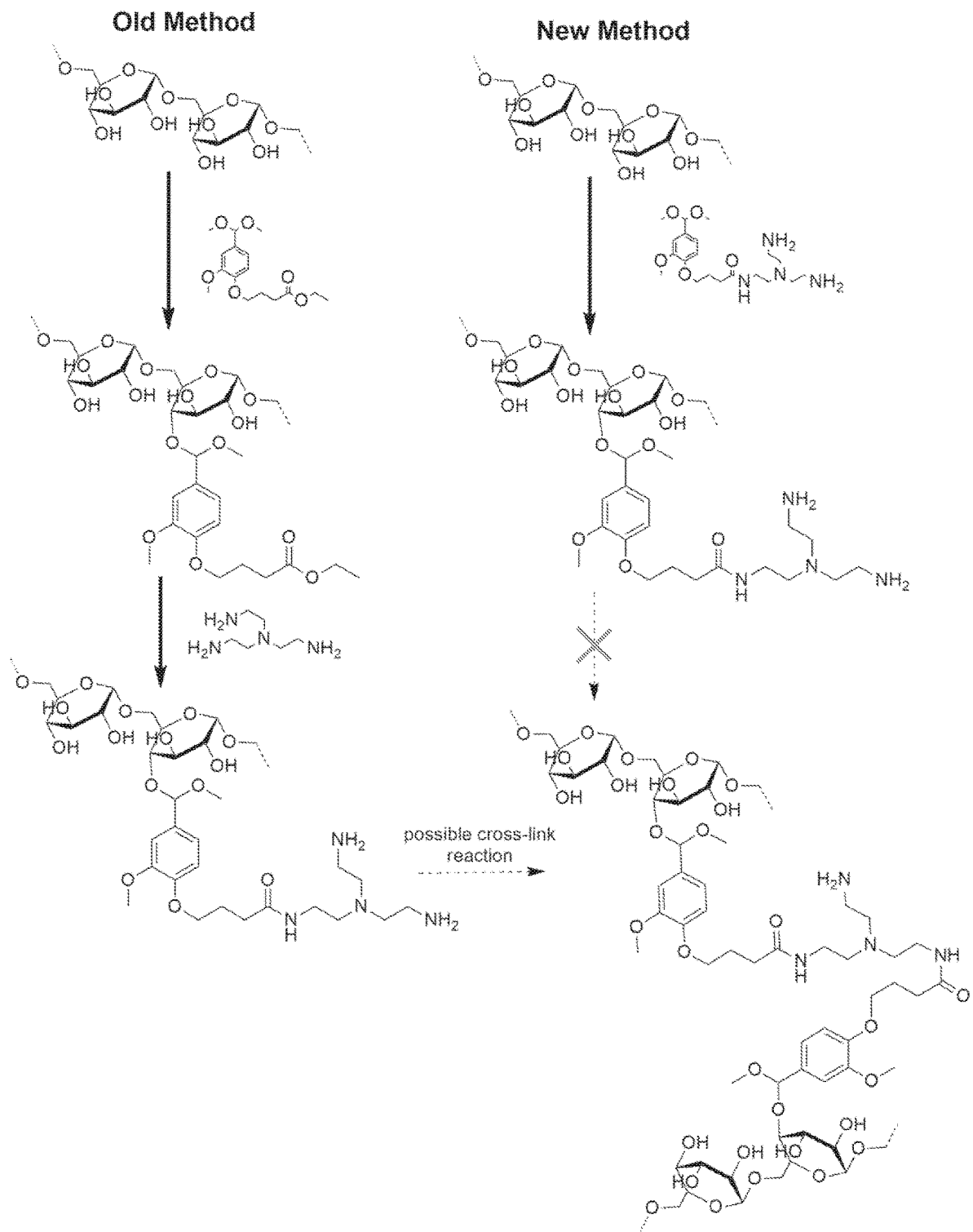
FIG. 12. Comparison of methods of synthesizing dextran. The method on the left doesn't use an optical imaging probe or labeled dextran. In addition, small molecules containing ester group are conjugated to the dextran through acetal bonds. Then the ester groups are able to react with polyamines to introduce amine groups to the dextran. This method allows the polyamines to continue to react with the ester groups of other dextran molecules resulting in cross-linking reactions. The method shown on the right (one embodiment of the present invention), illustrates using an optical imaging probe to synthesize dextran. The simple process of making dextran (having less steps than the process on the left) helps avoid problems of cross-linking reactions.

In molecular agent (cDNA, siRNA) delivery, release of the molecular agent from its carrier is critical to achieve successful transfection. Although the proton sponge hypothesis has been proposed as an advantage for effective endosomal escape of cationic polymer carriers, release of molecular agents from the carrier is equally important to achieve good transfection efficiency. In our dextran carrier, the amine groups were linked to the dextran scaffold though acetal bonds that were cleaved under weak acid conditions. With the cleavage of acetal bonds, the amine groups broke away from the dextran scaffold to release the molecular agent cargo. Degradation studies of compound 4 were performed at low and intermediate pH conditions (acetate buffer, pH 5.5 and PBS buffer, pH 7.4) using a colorimetric assay to detect Cy5.5 and rhodamine. The progress of degradation was monitored by comparing the ratio of the absorbance of rhodamine at 530 nm to the absorbance of Cy 5.5 at 670 nm. The Cy5.5 probe was conjugated to the dextran platform through the amide bond that was stable to variations of ph. As a result, the absorbance of Cy 5.5 showed very small variations at different pH buffers over time. Because rhodamine was conjugated to the amine group that was cleaved from the dextran scaffold under weak acid conditions, the absorbance of rhodamine decreased in pH 5.5 buffer over time. Since the compound was stable in pH 7.4 buffer, the ratio of the absorbance of rhodamine to the absorbance of Cy 5.5 should not show significant change at this pH. In contrast, at pH 5.5 buffer this ratio should decrease after removing the released dye by molecular weight cut-off centrifugation. As shown in FIG. 1D, in PBS buffer at pH 7.4 there was no obvious degradation and the absorbance ratios remained nearly constant up to 48 h of incubation. In contrast, amine groups were cleaved from the dextran scaffold at pH 5.5 starting at 2 h, and the absorbance of rhodamine decreased significantly as the incubation time progressed. These compounds were almost completely degraded after 48 h. Although aldehyde derivatives predominantly generate acyclic acetals that have a shorter half-life in water (pH 5.5 or pH 7.4) than their cyclic analogs, there were small amounts of more stable, difficult to cleave, cyclic acetal byproducts that caused weak absorbance of rhodamine after 48 h incubation in pH 5.5 acetate buffer. Results of the rhodamine to Cy 5.5 absorbance ratio in different pH buffers demonstrated that compound 4 was stable at pH 7.4 up to 7 days of (168 h) incubation, and was cleaved effectively under weak acid conditions of pH 5.5. This cleavage at pH 5.5 buffer was also confirmed by NMR spectroscopy (FIG. 10) and gel permeation chromatography (FIG. 11).

Mechanism of Nanoplex Cellular Internalization

Figures 2A, 2B:
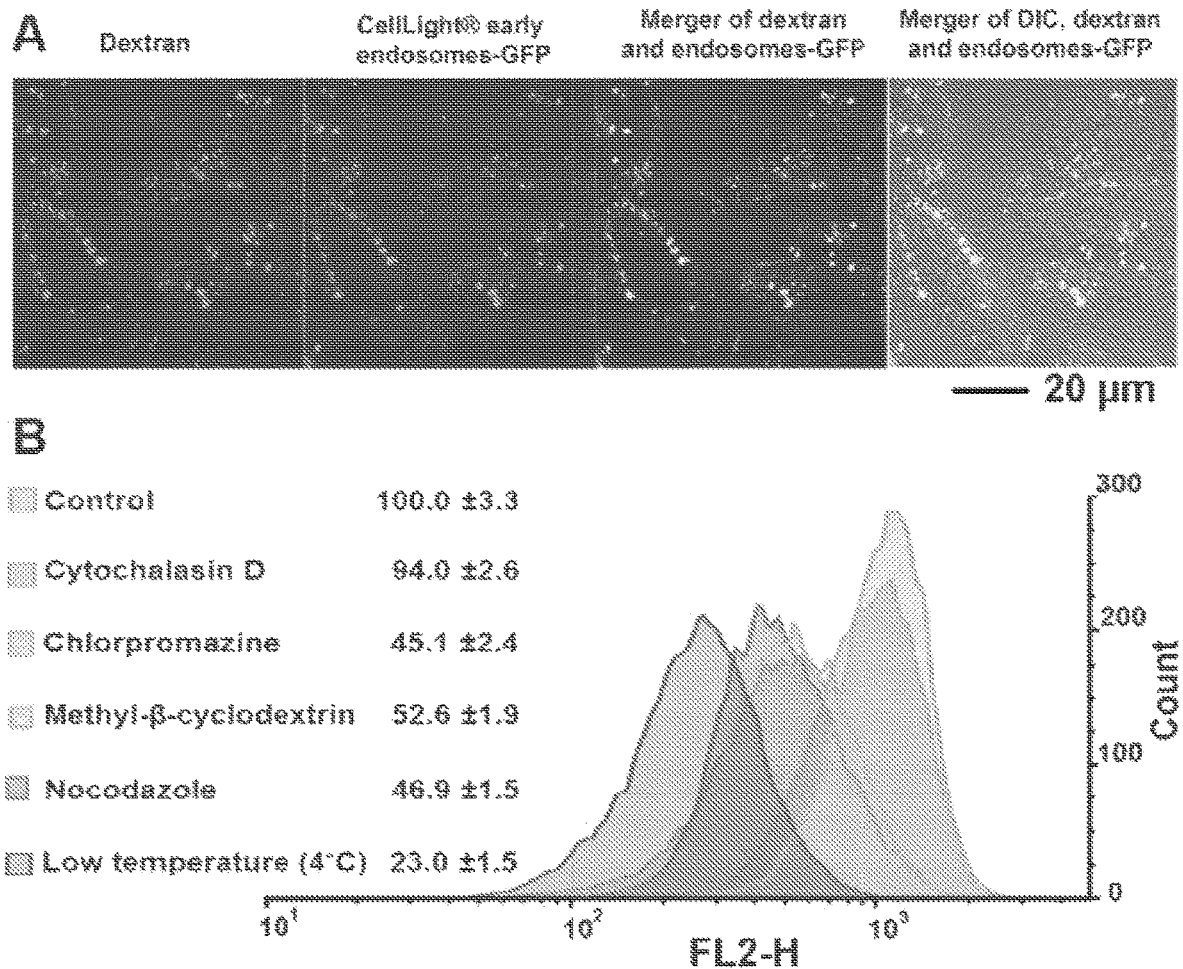
FIG. 2A-2B: (A) Representative laser confocal fluorescence microscopy fields of view image of MDA-MB-231 cells incubated for 1 h with siRNA/compound 4 nanoplex (red, rhodamine) and endosome marker (green, CellLight® Early Endosomes-GFP) (siRNA concentration: 20 nM; N/P ratio: 15). (B) Quantification of relative fluorescence intensity of the siRNA/compound 4 nanoplex in MDA-MB-231 human breast cancer cells treated with different endocytosis inhibitors (values represent mean±SD from three independent experiments).

Although several reports have identified the acetal bond as an acid sensitive bond that can be cleaved in weak acidic conditions this has only been demonstrated in buffer systems. Here, for the first time, we used multiple fluorescence reporters combined with imaging to investigate the fate of our dextran/siRNA nanoplex, including the intracellular distribution and cleavage of acetal bonds, in cells. In general, non-viral carriers enter cells through endocytosis vesicles. The carriers are trapped in early endosomes where the pH drops from neutral to around pH 6. More often, the delivery systems are trafficked to late endosomes that are rapidly acidified to pH 5-6 by the action of the membrane-bound ATPase proton-pump. Subsequently, the late endosomes fuse with lysosomes that are at pH 4.5 and contain several degradative enzymes. Endocytosis is therefore a key step for acid controlled degradation of our dextran/siRNA nanoplex because of the weak acid conditions that exist in endosomes. Evidence of the localization of our degradable dextran in endosomes would identify and confirm the degradation in cells in culture. The inventors therefore incubated MDA-MB-231 human breast cancer cells pretreated with CellLight® Early Endosomes-GFP, a fusion construct between Rab5a and GFP that specifically binds to early endosomes, with the siRNA/compound 4 nanoplex for 1 h. In FIG. 2A, the early endosomes-GFP can be observed in green, and most of the siRNA/compound 4 nanoplexes, detected by red fluorescence, were localized within these endosomes. These data indicated that this siRNA/compound 4 nanoplex localized in organelles that were weakly acidic in nature, a precondition required for rapid cleavage of acetal bonds.

The inventors further investigated the endocytosis pathway of siRNA/compound 4 nanoplex through quantification of the fluorescence intensity of the internalized nanoplex in the presence of endocytosis inhibitors. There are several different pathways for the endocytosis of particles, with specific inhibitors available to block these pathways to determine the effect on the nanoplex cellular uptake. The relative intensity of red fluorescence obtained by flow cytometry (normalized to intensity without inhibitor treatment) was measured to determine the amount of nanoplex uptake (FIG. 2B). Cytochalasin D was used to inhibit phagocytosis and micropinocytosis; chlorpromazine hydrochloride was used to inhibit clathrin mediated endocytosis; methyl-β-cyclodextrin was used to inhibit caveolae mediated endocytosis; and nocodazole was used as a microtubule-disrupting agent. Among these treatments, chlorpromazine hydrochloride, methyl-β-cyclodextrin and nocodazole demonstrated inhibition of the siRNA/compound 4 nanoplex uptake. A slight inhibition by cytochalasin D indicated that the uptake of the nanoplex was only mildly dependent on the phagocytosis and micropinocytosis pathways that are used to endocytose large particle (>100 nm). The significant reduction of fluorescence intensity at low temperature indicates an energy dependent uptake, and the absence of internalization through passive diffusion.

These data confirmed that the degradable nanoplex of the present invention entered cells through endocytosis, and localized within the endosome under weak acid conditions after entering cells. Localization in weak acidic cell organelles supported the possibility of degradation once the nanoplex was within cells. In FIG. 2A, the inventors detected strong fluorescence from the nanoplex within 1 h of incubation, indicating that this dextran nanopolymner with suitable introduction of amine groups could rapidly deliver siRNA within cells. The endocytosis pathway study also provided evidence of the size distribution of our nanoplex. Due to the novel synthesis method, the size distribution of the dextran was well controlled, and there were no large nanopolymers induced by crosslinking. Inhibition of phagocytosis and micropinocytosis pathways that are only used to endocytose large particles, did not modify uptake of the nanoplex.

Degradation of Nanoplex in Cells

Figure 3:
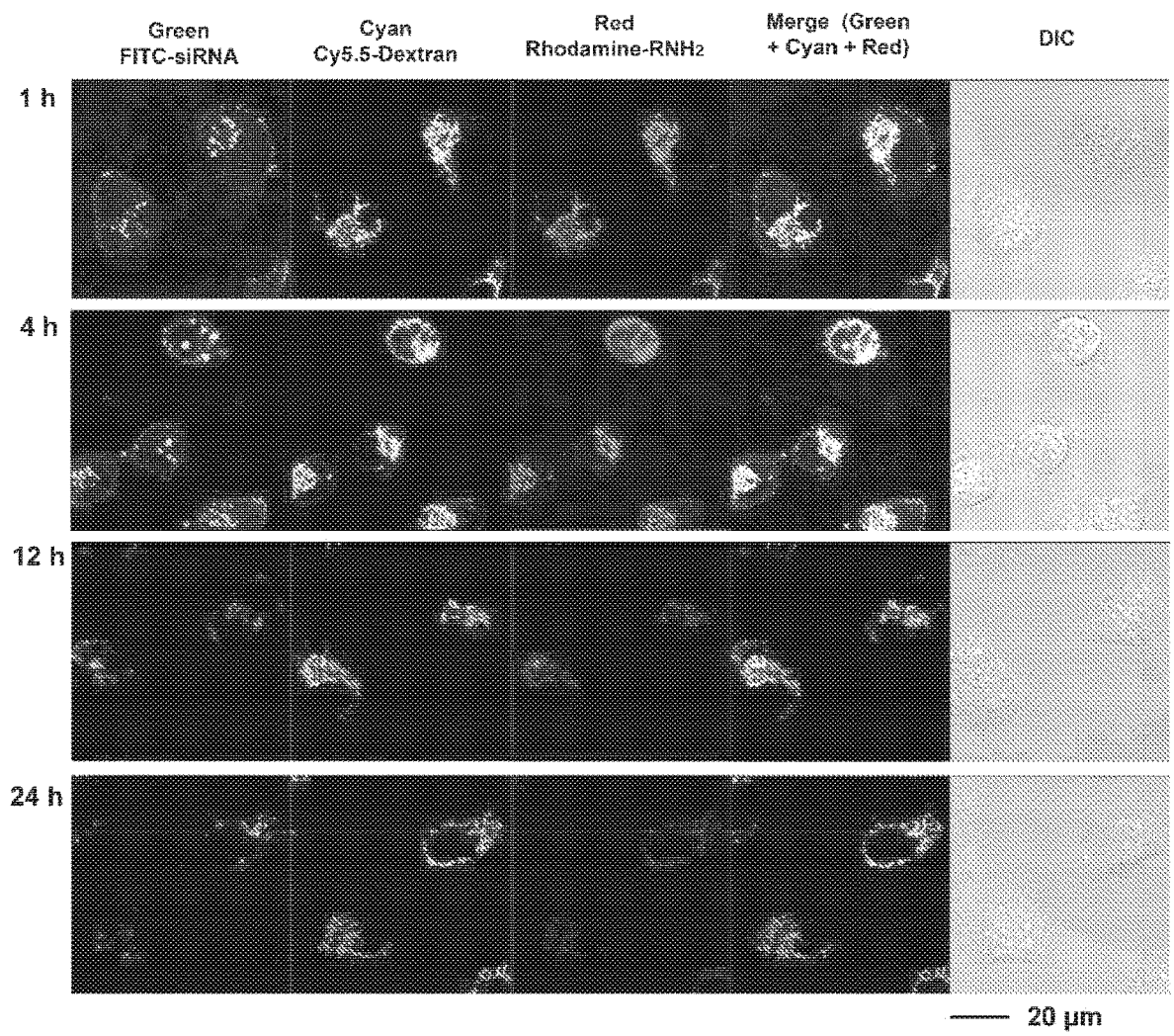
FIG. 3: Live-cell laser confocal fluorescence microscopy of living MDA-MB-231 cells with siRNA/compound 4 nanoplex. Cells were treated with FITC-siRNA/compound 4 nanoplex (concentration of siRNA: 100 nM; N/P ratio: 15).

Multi labeled imaging provided a means to visualize the degradation of the nanoplex in cultured cells. In compound 4, Cy 5.5 was conjugated to the dextran scaffold, rhodamine was labeled to the cleavable amine group, and the siRNA was labeled with FITC. Therefore, absence of co-localization of these dyes would indicate degradation of the siRNA nanoplex. Investigating the degradation of compound 4 in live cells was performed with laser scanning confocal microscopy (FIG. 3). Cells were treated with FITC labeled siRNA/compound 4 nanoplexes for 2 h, and then were further incubated in fresh medium at the times shown in FIG. 3. In FIG. 3, the fluorescence from FITC is displayed in green, the fluorescence from Cy5.5 labeled on the dextran scaffold is displayed in cyan, and the fluorescence from rhodamine labeled on cleavable amines is displayed in red. After 1 h of incubation in fresh medium, strong fluorescence was observed from FITC, Cy5.5 and rhodamine. Co-localization of fluorescence from Cy5.5 and rhodamine was clearly evident. Delocalized fluorescence of FITC indicated partly released siRNA. After 4 h of incubation in fresh medium, strong fluorescent signals from FITC, Cy5.5 and rhodamine were still observed but the absence of co-localized fluorescence of rhodamine and Cy 5.5 in the cytoplasm indicated that the acetal bonds had been cleaved, and free small molecules with amine groups were released into the cytoplasm. The changes of Mander's colocalization coefficients of Cy.5.5 and rhodamine (m1=0.901; m2=0.912 at 1 h, m1=0.921; m2=0.637 at 4 h) supported this absence of co-localization. At 12 h after treatment, a much weaker fluorescence of rhodamine, compared to fluorescence at 4 h, indicated that most acetal bonds had been cleaved. Because cleaved small molecules with amine groups are readily released from cells, the fluorescence intensity of rhodamine in the cytoplasm was very weak at 12 h. The amine groups were almost completed cleaved and removed from cells at 24 h after treatment, while the fluorescence of Cy5.5 that was conjugated to the dextran platform was still detected due to the slower metabolism of the larger sized dextran scaffold.

These imaging data indicated that the amine groups conjugated to the dextran scaffold through the acetal bonds were cleaved in endosomes under weak acidic condition. The increased delocalization of the siRNA (green color) and dextran scaffold (cyan color) proved that the cleavage of amine groups caused efficient release of siRNA from the nanoplex. The rapid release of cleaved small molecules with amine groups from cells was identified from the elimination of red fluorescence. Therefore, the side-effects of these small molecules were minimized. Although the imaging results showed the dextran scaffolds could be retained in the cells for a longer time compared with the small amine molecules, they did not induce inflammation due to their high biocompatibility.

Downregulation of COX-2 in Cells

Figure 4A:
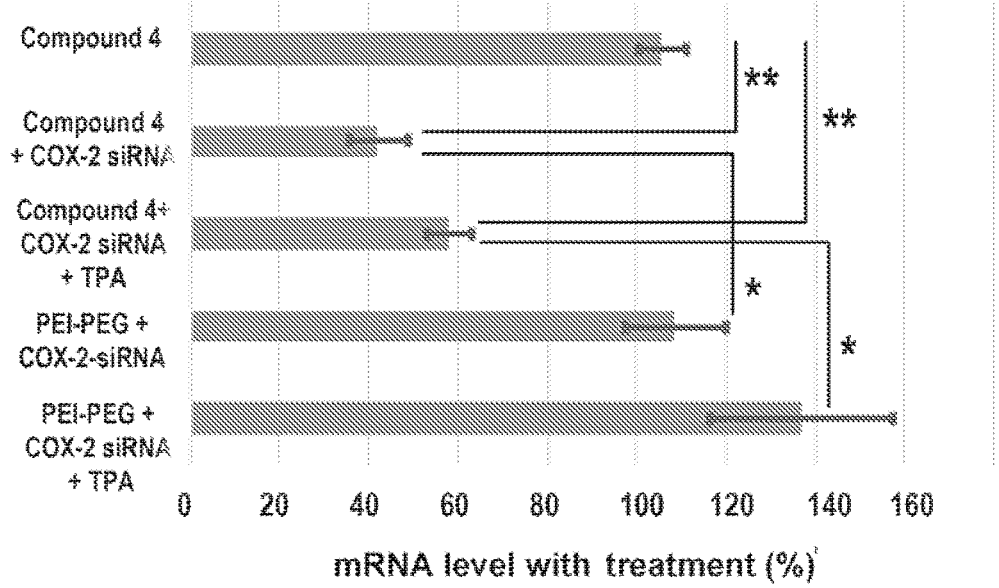
FIG. 4A-4B: (A) Changes in mRNA levels in MDA-MB-231 cells following different siRNA treatments. (siRNA concentration: 100 nM; N/P ratio: 15. Cells were treated with siRNA-dextran for 8 h, following which the medium was replaced with fresh medium for a further incubation of 24 h before collection, 12-O-tetradecanoylphorbol-13-acetate (TPA) treated cells were incubated with 10 ng/mL TPA to induce COX-2 6 h before collection, and incubated for a further 24 h. Values represent mean±SD (n=3). \*\*: P<0.01, \*: P<0.05. mRNA levels were normalized to untreated cells. (B) $PGE_2$ expression in MDA-MB-231 cells: MDA-MB-231 cells were treated with COX-2 siRNA/compound 4 nanoplex (N/P=15 for dextran; COX-2 siRNA concentration: 100 nM). Values represent Mean±SD from three biological experiments. \*\*p≤0.01, n=3).

Treatment with COX-2 siRNA should decrease COX-2 expression levels, but established artificial cationic polymer carriers enhanced COX-2 expression and were found to be proinflammatory. A cationic polymer carrier that induces minimal inflammation is critically important for delivering COX-2 siRNA to achieve effective downregulation. Quantitative reverse transcription polymerase chain reaction (qRT-PCR) was performed to measure COX-2 expression in MDA-MB-231 human breast cancer cells (FIG. 4A). Cells were treated with COX-2 siRNA/compound 4 nanoplex for 8 h, after which the medium containing the released amines was replaced with fresh medium. After 24 h of further incubation, cells were collected and processed for quantitative real-time polymerase reaction (qRT-PCR) assay to determine messenger RNA (mRNA). In some experiments 12-O-tetradecanoylphorbol-13-acetate (TPA) was added to the fresh medium to induce COX-2 expression at 6 h before cell harvest. As shown in FIG. 4A, when PEI-PEG, an ordinary cationic polymer transfection agent, and Lipofectamine™ 2000, which is a commercial transfection agent, were chosen to deliver COX-2 siRNA there was no decrease in COX-2 mRNA levels. Instead, following treatment with COX-2 siRNA with PEI-PEG, the level of COX-2 significantly increased to 139% (with TPA induction) or 109% (without TPA induction) compared to COX-2 mRNA levels without siRNA treatment. The commercial transfection agent Lipofectamine™ 2000 showed similar results as PEI. In contrast, our degradable compound 4 with COX-2 siRNA demonstrated significant inhibition of COX-2 expression. After COX-2 siRNA/compound 4 nanoplex treatment, the level of COX-2 decreased to 58% (with TPA induction) or 42% (without TPA induction) of COX-2 level without siRNA treatment.

Figure 4B:
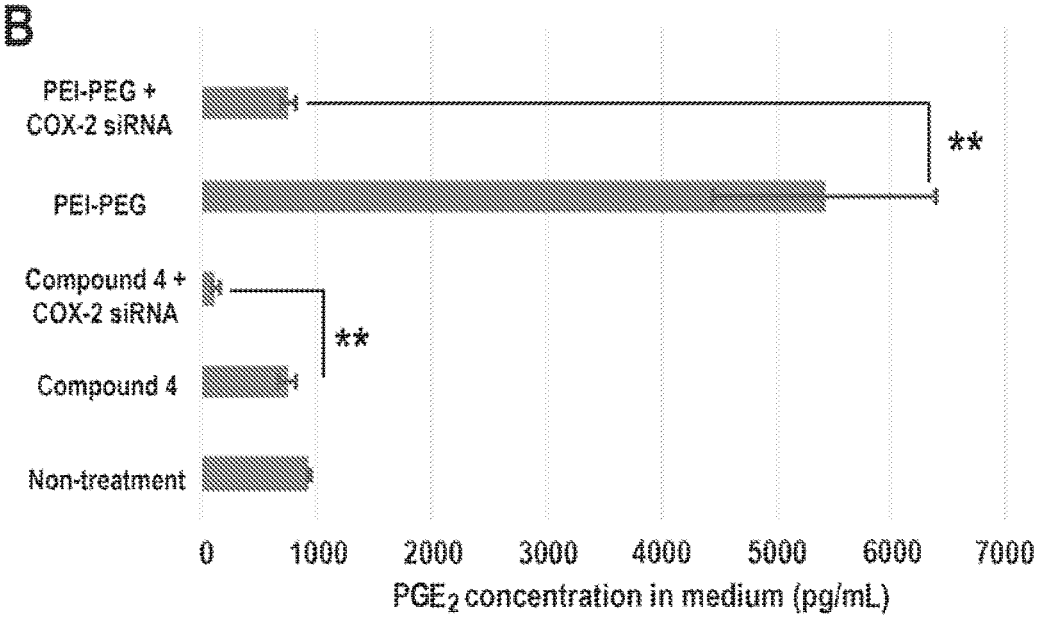

The cyclooxygenase activity of COX catalyzes the formation of prostaglandin $G_2$ ($PGG_2$), an unstable intermediate that is quickly converted to prostaglandin $H_2$ ($PGH_2$) by the peroxidase activity of the enzyme. From this precursor, PGE synthase initiates the production of $PGE_2$. Its activity influences inflammation, fertility, immune modulation, and promotes cancer cell growth, survival, and angiogenesis. Decreased expression of COX-2 should lead to a reduction of $PGE_2$. We therefore investigated $PGE_2$ concentration in cell culture medium following different treatments (FIG. 4B). Compared with $PGE_2$ concentration in the medium without treatment, we found that the dextran compound 4 did not affect $PGE_2$ concentration. When we treated MDA-MB-231 human breast cancer cells with COX-2 siRNA/compound 4 nanoplex, $PGE_2$ concentration in the medium significantly decreased to 126 pg/mL, which was 15% of the concentration with compound 4 treatment without siRNA. In contrast, following treatment with PEI-PEG, $PGE_2$ concentration in medium increased significantly to approximately 5400 pg/mL. Because the PEI-PEG carrier increased $PGE_2$ concentration, the COX-2 siRNA/PEI-PEG nanoplex was unable to reduce $PEG_2$ concentration.

As mentioned earlier, there are few if any reports about cation polymers as carriers for COX-2 siRNA delivery. Here we used PEGylated PEI, a common cationic polymer applied in siRNA transfection as a control. PEI increased the expression of COX-2 to such an extent that it offset downregulation caused by siRNA. Our degradable compound 4 was cleaved to release amine groups with positive charge. Compared to macromolecules, the small molecules with amine groups were rapidly removed from cells. These detached amine groups were distributed more uniformly in the cytoplasm, which reduced positive charge density. Due to high biocompatibility, although the dextran scaffold was depolymerized to small molecules by α-1-glucosidases present in cells and various organs, their retention in cells did not affect COX-2 expression. Consequently, our degradable compound 4 minimized inflammation, and was able to downregulate COX-2 successfully.

In Vivo and Ex Vivo Imaging of siRNA/Compound 4 Nanoplex in Tumors

Figures 5A, 5B, 5C:
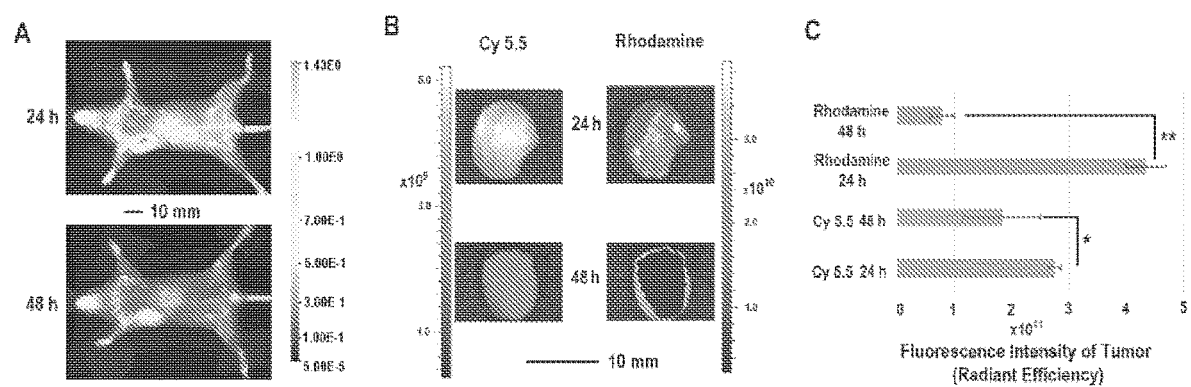
FIG. 5A-5C: (A) Representative longitudinal in vivo Cy5.5 NIR fluorescence optical images of a SCID mouse bearing an MDA-MB-231 tumor. Mice were injected with nanoplex (compound 4: 2.0 mg/mouse, N/P=15; COX-2 siRNA: 4 nmol/mouse) through the tail vein. (B) Representative ex vivo Cy5.5 and rhodamine fluorescence optical images of MDA-MB-231 tumors at 24 h and 48 h. (C) Quantification of Cy 5.5 and rhodamine fluorescence intensity from ex vivo tumors. (\*\* P<0.01, \* P<0.05, values represent mean±SD, n=3).

The in vivo distribution of COX-2 siRNA/compound 4 nanoplex was analyzed by fluorescence imaging of Cy 5.5 (FIG. 5A). Strong accumulation of the nanoplex in orthotopically implanted MDA-MB-231 tumors was observed at 24 h post injection, while fluorescence from Cy 5.5 was observed in the liver and kidney. At 48 h post injection, accumulation of nanoplex in tumors slightly decreased compared to the 24 h time point. Accumulation of the nanoplex in tumors detected by imaging strongly indicated that the carrier could effectively deliver COX-2 siRNA within tumors. Because the fluorescence of rhodamine could not penetrate the tissue and skin, in vivo imaging could not confirm degradation of the dextran carrier in tumors in vivo. We therefore performed ex vivo imaging to identify degradation of compound 4 in tumors. In FIG. 5B, fluorescence imaging at 24 h after injection detected strong signals from both Cy 5.5 and rhodamine. At 48 h after injection, the fluorescence from Cy 5.5 and rhodamine was weaker than at 24 h after injection. Decrease of the fluorescence intensity of rhodamine at 48 h was, however, more significant than Cy 5.5. FIG. 5C displays quantification of the ex vivo fluorescence intensity. The fluorescence intensity of Cy 5.5 was 2.74 at 24 h, and decreased to 1.84 (67% of the value at 24 h) at 48 h. In contrast, the fluorescence of rhodamine was 4.33 at 24 h, and decreased to 0.79 (18% of the value at 24 h) at 48 h.

The enhanced permeability and retention (EPR) effect in solid tumors is a characteristic that facilitates tumor specific delivery of macromolecules. Because of high tumor vascular permeability, macromolecules accumulate in solid tumors. The size of the COX-2 siRNA/compound 4 nanoplex with a diameter of ~20 nm was ideal for the EPR effect, allowing significant accumulation of the nanoplex, as observed in FIG. 5A. The prolonged retention time of the dextran scaffold caused a slow decrease of the fluorescence of Cy 5.5 as shown in FIGS. 5B and 5C. The acidic environment within endosomes facilitated cleavage of the acetal bonds linking the amine groups to the dextran scaffold. Once the small amine groups were cleaved, they were rapidly metabolized compared to the dextran scaffold. Since rhodamine was only labeled on the small molecules with amine groups, rhodamine clearance was also more rapid than Cy 5.5 that was attached to the dextran scaffold. A small amount of acyclic acetal bonds that were not cleaved resulted in some fluorescence from rhodamine, even 48 h after injection, in tumor tissues.

Downregulation of COX-2 in Tumors

Figures 6A, 6B:
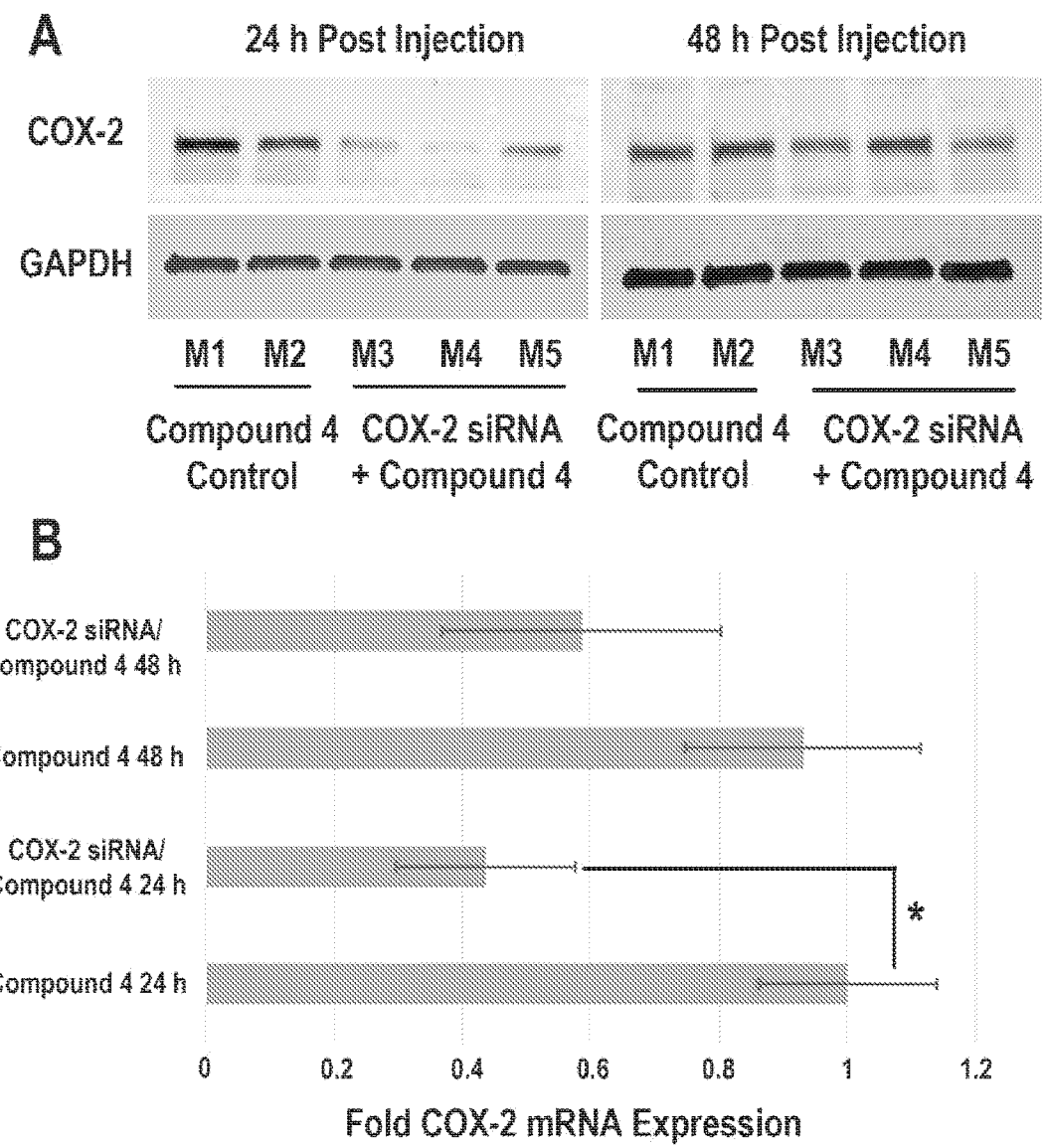
FIG. 6A-6B: (A) Representative immunoblot assays of COX-2 protein expression in MDA-MB-231 tumors obtained from different mice (M). Mice were injected with siRNA/compound 4 nanoplex (compound 4: 2.0 mg/mouse, N/P=15; COX-2 siRNA: 4 nmol/mouse) through the tail vein. (B) Fold mRNA levels in MDA-MB-231 tumors following different treatments. Concentration of siRNA/compound 4 nanoplex: compound 4, 2.0 mg/mouse, N/P=15; COX-2 siRNA, 4 nmol/mouse; values represent mean±SD, n=3. \*: P<0.05.

Downregulation of COX-2 achieved by siRNA/compound 4 nanoplex in MDA-MB-231 tumors is presented in FIG. 6. In the immunoblot results (FIG. 6A), at 24 h after injection, all tumors treated with COX-2 siRNA/compound 4 nanoplex demonstrated significant downregulation of COX-2 expression. At 48 h post injection, a trend towards lower COX-2 expression continued. The difference in COX-2 expression between 24 and 48 h post injection could be due to the half-life of the unmodified siRNA in the nanoplex, presence of nucleases in the tumor microenvironment, and dilution of signal in the dividing tumor cells. To further validate this difference, qRT-PCR was performed to measure in vivo COX-2 mRNA levels in tumors (FIG. 6B). The fold mRNA expression was normalized to the expression of 24 h treatment of compound 4 alone. With COX-2 siRNA treatment, mRNA expression decreased to 0.43-fold of expression without treatment at 24 h post treatment compared to 0.59-fold at 48 h. These results demonstrate that our degradable dextran compound 4 could effectively deliver COX-2 siRNA into tumors and downregulate the expression of COX-2. However continued dosing may be required to achieve sustained downregulation over longer periods of time. Because of the rapid degradation of the dextran nanopolymer, COX-2 siRNA was quickly released inducing downregulation of COX-2 protein and mRNA expression within 24 h.

In summary, we have developed an efficient method to produce an acid-degradable dextran nanopolymer containing cleavable amine groups as the siRNA carrier. The synthesis method allowed modifications of the dextran scaffold for conjugating multiple functional molecules, such as imaging reporters or targeting moieties. This degradable dextran compound is stable under neutral pH conditions, but under weak acid conditions, such as in endosomes, acid labile acetal bonds are cleaved, rapidly releasing the amine groups and siRNA. Cellular localization and degradation of this compound was observed through cell imaging. The labeled fluorescence probes also allowed identification of endocytosis as a pathway of the uptake of this dextran/siRNA nanoplex. The cleavage and release of amine groups did not increase COX-2 expression, unlike other cationic polymer carriers that induced COX-2 expression. This degradable dextran as a cationic polymer siRNA carrier delivered COX-2 siRNA within tumors and efficiently downregulated COX-2 expression. To the best of the inventors' knowledge, this is the first report describing the use of a cationic polymer as a successful COX-2 siRNA carrier to effectively downregulate COX-2 in cancer cells and in tumors. Because of its biocompatibility and synthesis reproducibility, this siRNA carrier has a clear path for translational applications to achieve effective COX-2 or other pharmaceutical agent delivery, including siRNA, in patients.

Embodiments of the disclosure concern methods and/or compositions for the delivery of agents using dextran nanopolymers of the present invention as carriers to treat disease. For example, the dextran nanopolymers of the present invention may carrier pharmaceutical agents capable of treating and/or preventing cancer including cancers of the colon, esophagus, lung, bladder, breast and prostate, including COX-2 inhibitors. In certain embodiments, individuals with cancer are treated with a pharmaceutical composition comprising dextran nanopolymers of the present invention including a pharmaceutical agent, such as a siRNA. An example of a siRNA pharmaceutical agent is a COX-2 inhibitor. Subjects administered one or more pharmaceutical compositions of the present invention see inhibition of cancer growth when compared to subjects with cancer who were not administered pharmaceutical compositions of the present invention. In other embodiments the methods of the present invention (including dextran nanopolymers) may treat or prevent any disease that would benefit from COX-2 down regulations when the delivery compositions (dextran nanopolymers) of the present invention include COX-2 inhibitors.

In certain embodiments, the level to which a composition of the present decreases cancer growth may be any level so long as it provides amelioration of at least one symptom of the cancer. The level of expression may increase by at least 2, 3, 4, 5, 10, 25, 50, 100, 1000, or more fold expression compared to the level of expression in a standard, in at least some cases. An individual may monitor cancer growth using standard methods in the art, such as northern assays or quantitative PCR, for example.

An individual known to have cancer, suspected of having cancer, or at risk for having cancer may be provided an effective amount of a dextran nanopolymers of the present invention comprising a pharmaceutical agent such as a cancer inhibitor. For example, pharmaceutical agent may be a siRNA agent, such as a COX-2 inhibitor. Those at risk for cancer may be those individuals having one or more genetic factors, may be of advancing age, and/or may have a family history, for example.

In particular embodiments of the disclosure, an individual is given an agent, such as a cancer treatment, in addition to the one or more dextran nanopolymers of the present invention comprising agents to treat disease, such as cancer. Such additional therapy may include one or more chemotherapy agents, for example. When combination therapy is employed with one or more dextran nanopolymers of the present invention comprising agents to treat disease, the additional therapy may be given prior to, at the same time as, and/or subsequent to the present compositions or carriers comprising agents to treat disease.

Pharmaceutical Preparations

Pharmaceutical compositions of the present invention comprise one or more dextran nanopolymers of the present invention and an effective amount of one or more pharmaceutical agents such as an agent that treats or prevents cancer, as an example. The pharmaceutical agent may be a peptide, protein, chemical, or a nucleic acid. The pharmaceutical compositions of the present invention maybe dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that comprises at least one dextran nanopolymer of the present invention including an pharmaceutical agent, such as a cox2 inhibitor, will be known to those of skill in the art in light of the present disclosure, as exemplified by Remington: The Science and Practice of Pharmacy, 21$^{st}$ Ed. Lippincott Williams and Wilkins, 2005, incorporated herein by reference. Moreover, for animal (e.g., human) administration, it will be understood that preparations should meet sterility, pyrogen city, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The one or more dextran nanopolymers of the present invention comprising an pharmaceutical, may comprise additional carriers depending on whether it is to be administered in solid, liquid or aerosol form, and whether it need to be sterile for such routes of administration as injection. The present compositions can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The one or more pharmaceutical agents of the present invention, such as a COX2 inhibitor, may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present disclosure, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof. In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include one or more dextran nanopolymers of the present invention one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

Alimentary Compositions and Formulations

In one embodiment of the present disclosure, the compositions of the present invention are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792,451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present disclosure may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Parenteral Compositions and Formulations

In further embodiments, compositions of the present invention may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,7537,514, 6,613,308, 5,466,468, 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by FDA Office of Biologics standards.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

Miscellaneous Pharmaceutical Compositions and Formulations

In other preferred embodiments of the invention, one or more dextran nanopolymers of the present invention and an active compound such as a cancer or COX 2 inhibitor (as an example) may be formulated for administration via various miscellaneous routes, for example, topical (i.e., transdermal) administration, mucosal administration (intranasal, vaginal, etc.) and/or inhalation. Pharmaceutical compositions for topical administration may include the active compound formulated for a medicated application such as an ointment, paste, cream or powder. Ointments include all oleaginous, adsorption, emulsion and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

Kits of the Disclosure

Any of the compositions described herein may be comprised in a kit. In a non-limiting example, one or more dextran nanopolymers of the present invention and/or an agent such as a COX 2 inhibitor (for example, a siRNA of the present invention) may be comprised in a kit.

The kits may comprise a suitably aliquot of one or more dextran nanopolymers of the present invention, one or more agents, and, in some cases, one or more additional agents. The component(s) of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the compositions of the present invention and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. The compositions of the present invention may be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means.

METHODS/EXAMPLES

The following Methods/Examples have been included to provide guidance to one of ordinary skill in the art for practicing representative embodiments of the presently disclosed subject matter. In light of the present disclosure and the general level of skill in the art, those of skill can appreciate that the following Methods/Examples are intended to be exemplary only and that numerous changes, modifications, and alterations can be employed without departing from the scope of the presently disclosed subject matter. The following Methods/Examples are offered by way of illustration and not by way of limitation.

Degradation of Compound 4 in Different pH Buffers

Compound 4 (2 mg) was dissolved in 2 mL buffer (pH 5.5 or pH 7.4) and incubated for the desired time. After incubation, the free cleaved amine molecules with rhodamine were removed by molecular weight cutoff centrifugation (Amicon ultra-15, 10,000 MW cutoff). Three further centrifugations in PBS (pH 7.4) buffer were performed to remove free rhodamine completely. Absorbances at 530 nm and 670 nm were recorded.

Cell Culture

MDA-MB-231 human breast cancer cells were obtained from American Type Culture Collection (ATCC) (Manassas, VA). Fetal bovine serum, penicillin, and streptomycin were purchased from Invitrogen (Carlsbad, CA). Cells were maintained in RPMI 1640 (Invitrogen, Grand Island, NY) supplemented with 10% fetal bovine serum in a humidified incubator at 37° C./5% $CO_2$. Cells were seeded at a density of 400,000 cells per dish in a 6 cm dish (for RT-PCR experiments) or 20,000 cells per well in a 4-well slide chamber (for confocal laser scanning fluorescence microscopy studies) 24 h prior to the transfection experiment.

Localization of Compound 4/siRNA Nanoplex in Endosomes

MDA-MB-231 cells seeded in a 4-well cover glass chamber were treated with CellLight® Early Endosomes-GFP (Thermo Fisher Scientific, Waltham, MA) for 24 h. Then compound 4/siRNA nanoplex (concentration of compound 4: 1 µg/mL; N/P=15) was added for 1 h of incubation. After incubation, the transfection mixture was removed, and cells were washed twice with fresh medium. Fluorescence microscopy images of MDA-MB-231 cells were generated on a Zeiss LSM 700 META confocal laser-scanning microscope (Carl Zeiss, Inc. Oberkochen, Germany).

Quantification of Relative Fluorescence Intensity of Compound 4 Nanoplex in MDA-MB-231 Cells Treated with Different Endocytosis Inhibitors MDA-MB-231 cells seeded in 6 cm dishes at 60% confluence were treated with endocytosis inhibitors (cytochalasin D: 5 µg/mL; chlorpromazine hydrochloride: 5 µg/mL; methyl-β-cyclodextrin: 6 mg/mL; nocodazole: 6 mg/mL), or incubated at 4° C., for 45 min. Then siRNA/compound 4 nanoplex (siRNA concentration: 100 nM) was added to the solution for a further 2 h incubation under the same conditions. After incubation, cells were harvested, washed, and fixed for quantification of fluorescence intensity. Quantification of fluorescence intensity of dextran uptake was performed by BD FACSCalibur flow cytometry (BD Biosciences, San Jose, CA)

In Vitro Imaging of Degradation of siRNA Nanoplex

MDA-MB-231 cells seeded in 4-well coverglass chambers were treated with siRNA/compound 4 nanoplex (siRNA concentration: 100 nM) for 2 h. After treatment, this medium was replaced by fresh medium for further incubation and investigation. Fluorescence microscopy images of MDA-MB-231 cells were generated on a Zeiss LSM 700 META confocal laser-scanning microscope.

COX-2 qRT-PCR Assay and $PGE_2$ ELISA of MDA-MB-231 Cells

The siRNA/compound 4 nanoplex in RPMI 1640 medium solution (concentration of siRNA: 100 nM, N/P=15) was added to each dish for 8 h incubation. After incubation, cells were incubated in fresh medium for a further 16 h. In TPA treatment experiments, TPA was added to medium at 6 h before harvest. Before harvesting the cells, the supernatant of cell culture medium was collected, and $PGE_2$ ELISA was performed following instructions provided by the manufacturer (Cayman Chemical, Ann Arbor, MI). ELISA was performed in triplicates. Total RNA was isolated from cells by using QIA shredder and RNeasy Mini kit (Qiagen, Valencia, CA, USA) according to the manufacturer's protocol. The expression of target RNA relative to the housekeeping gene HPRT1 was calculated based on the threshold cycle (Ct) as $R=2^{-\Delta(\Delta Ct)}$, where ΔCt=Ct of target−Ct of HPRT1. Primer for COX-2 was purchased from Qiagen (Cat. No. QT00040586). The following primers against HPRT1-the house keeping gene-Fwd-5'-CCTGGCGTCGT-GATTAGTGATG-3' and Rev-5'-CAGAGGGCTA-CAATGTGATGGC-3' were designed using either Beacon designer software 7.8 (Premier Biosoft, Palo Alto, CA, USA) or a free web-based software Primer3Plus software (Premier Biosoft, Palo Alto, CA, USA).

Mouse Model and Tumor Implantation.

All in vivo studies were done in compliance with guidelines established by the Institutional Animal Care and Use Committee of the Johns Hopkins University. MDA-MB-231 human breast cancer cells ($2\times10^6$ cells/mouse) were inoculated subcutaneously in the mammary fat pad of female severe combined immunodeficient (SCID) mice. Tumors were palpable within two weeks after implantation and reached a volume of ~300-400 $mm^3$ within four to five weeks, at which time they were used for the studies.

In Vivo and Ex Vivo Optical Imaging Studies

In vivo optical images were acquired with a Pearl® Trilogy Small Animal Imaging System (LI-COR, Lincoln, NE), ex vivo optical images were acquired with an IVIS Lumina Series III Spectrum scanner (Perkin-Elmer, Waltham, MA), and fluorescence intensities in regions of interest (ROIs) were quantified by using Living Image 4.5 software (Caliper, Hopkinton, MA). For in vivo optical imaging of the distribution of COX-2 siRNA/compound 4 nanoplex, MDA-MB-231 tumor bearing mice were injected intravenously with 100 μL of dextran conjugated COX-2 siRNA nanoplex (dextran 2.0 mg/mouse, N/P=20. COX-2 siRNA, 4 nmol/mouse) through the tail vein. Delivery of the nanoplex was confirmed by imaging the mice at 24 h and 48 h. Subgroups of mice were sacrificed either at 24 h and/or at 48 h after nanoplex injection for ex vivo imaging studies, and tumors and muscle were excised to obtain the optical images.

In Vivo Downregulation of COX-2 Expression

After imaging, tumors were excised at each time point and freeze clamped for molecular analysis. cDNA was synthesized from RNA isolated from the frozen samples. Total RNA was isolated from tumor tissues by using QIA shredder and RNeasy Mini kit according to the manufacturer's protocol. Hypoxanthine phosphoribosyl transferase 1 (HPRT1) was used as a housekeeping gene for internal control. In the immunoblot analysis of tumor tissues, proteins were extracted using RIPA buffer with protease inhibitor cocktail (1/500, Sigma, St. Louis, MO), dithiothreitol (1/1,000, 1 M stock), phenylmethylsulfonyl fluoride (1/200, 0.2 M stock), sodium orthovanadate (1/500, 0.5 M stock) and sodium fluoride (1/500, 0.5 M stock). Protein was isolated and quantified from each tumor. 60 μg of protein was resolved on 4-15% gradient SDS gel. Proteins were transferred to a nitrocellulose membrane overnight at 40° C. The membrane was immunoblotted against goat polyclonal anti-COX-2 antibody. Antibody against glyceraldehyde 3-phosphate dehydrogenase (GAPDH) was used as a loading control.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A delivery composition comprising:
   a collection of polysaccharide degradable dextran nanopolymers comprising one or more amines attached to the dextran nanopolymers with a linker comprising an acetal, wherein the collection of nanopolymers comprises 25% or less cross linking, wherein at least one non-terminal glucose residue of a dextran scaffold of a given nanopolymer comprises one or more first imaging reporters, wherein at least one of the one or more amines of the given nanopolymer comprises one or more second imaging reporters, and wherein the first and second imaging reporters differ from one another such that upon cleavage of the amines from the dextran scaffold of the given nanopolymer, a degradation, distribution, and/or metabolism of the amines and the dextran scaffold can be visualized by optical imaging.

2. The delivery composition of claim 1 further comprising spheres of the polysaccharide degradable dextran nanopolymers with a radius in the range of 5 nm to 100 nm.

3. The delivery composition of claim 1 wherein the collection of polysaccharide degradable dextran nanopolymers is positively charged.

4. The delivery composition of claim 1 further comprising a negatively charged agent that binds electrostatically with one or more amine groups on the nanopolymers.

5. The delivery composition of claim 4 wherein the agent is a nucleic acid, drug compound, protein, antibody, peptide, or a combination thereof.

6. The delivery composition of claim 4 wherein the agent is a siRNA.

7. The delivery composition of claim 6 wherein the siRNA is a cyclooxygenase-2 (COX-2) siRNA.

8. The delivery composition of claim 1 comprising a pharmaceutically acceptable carrier.

9. The delivery composition of claim 1 wherein one or more of the nanopolymers comprise a targeting moiety.

10. The delivery composition of claim 1 wherein the first imaging reporters comprise a cyanine dye and wherein the second imaging reporters comprise a rhodamine dye.

11. The delivery composition of claim 1 wherein the dextran scaffold of the given nanopolymer comprises multiple first imaging reporters.

12. A method of delivering a negatively charged agent to a cell comprising the steps of:
   administering a pharmaceutical composition comprising a collection of nanopolymers of polysaccharide comprising one or more amines attached to the nanopolymers with a linker comprising an acetal and said agent, wherein the collection of nanopolymers comprises 25% or less cross linking, wherein at least one non-terminal glucose residue of a dextran scaffold of a given nanopolymer comprises one or more first imaging reporters, wherein at least one of the one or more amines of the given nanopolymer comprises one or more second imaging reporters, and wherein the first and second imaging reporters differ from one another such that upon cleavage of the amines from the dextran scaffold of the given nanopolymer, a degradation, distribution, and/or metabolism of the amines and the dextran scaffold can be visualized by optical imaging.

13. The method of claim 12 wherein a tumor comprises the cell and the growth of the tumor in a subject is inhibited.

14. The method of claim 13 wherein COX-2 expression is downregulated in the tumor.

\* \* \* \* \*